United States Patent [19]

Knoblich

[11] Patent Number: 5,069,219
[45] Date of Patent: Dec. 3, 1991

[54] SELF SNUGGING UNIVERSAL BLOOD PRESSURE CUFF

[75] Inventor: Stanley M. Knoblich, Everett, Wash.
[73] Assignee: SpaceLabs, Inc., Redmond, Wash.
[21] Appl. No.: 454,025
[22] Filed: Dec. 20, 1989
[51] Int. Cl.[5] .............................................. A61B 5/022
[52] U.S. Cl. ................................... 128/679; 128/686; 606/202
[58] Field of Search ............... 128/672, 677, 674, 680, 128/682, 686, 715; 606/202, 203, 204

[56] References Cited

U.S. PATENT DOCUMENTS

| | | | |
|---|---|---|---|
| 3,935,984 | 2/1976 | Lichowsky et al. | 128/686 |
| 4,501,280 | 2/1985 | Hood | 128/686 |
| 4,799,492 | 1/1989 | Nelson | 128/672 |
| 4,920,971 | 5/1990 | Blessinger | 128/679 |
| 4,938,226 | 7/1990 | Danielsson et al. | 128/678 |

OTHER PUBLICATIONS

News from the American Heart Association, 1981, vol. 12, Recommendations for Human Blood Pressure Determinatino by Sphygmomanometers by Walter M. Kirkendall, M.D., Manning Feinleib, M.D., Edward D. Freis, M.D. and Allyn L. Mark, M.D.

Primary Examiner—William E. Kamm
Assistant Examiner—Scott R. Akers
Attorney, Agent, or Firm—Seed and Berry

[57] ABSTRACT

A blood pressure cuff formed by a cylindrical envelope of flexible, non-resilient, air-impermeable material. The envelope is divided into two circumferentially spaced sections that are isolated from each other thereby forming two separate bladders each of which may be separately inflated. One bladder is inflated to snug the cuff around the arm of a patient while the other bladder is used to make a blood pressure measurement in a conventional manner.

10 Claims, 2 Drawing Sheets

SELF SNUGGING UNIVERSAL BLOOD PRESSURE CUFF

FIELD OF THE INVENTION

This invention relates to blood pressure cuffs for making blood pressure measurements, and, more particularly, to a blood pressure cuff that can be automatically made snug around the arm of a patient regardless of the circumference of the patient's arm.

BACKGROUND ART

Blood pressure measurements are one of the most commonly performed medical tests. Blood pressure measurements are typically mad by snugly wrapping a blood pressure cuff around the arm of a patient and fastening it in place. The cuff is then connected to a manometer or automatic blood pressure monitor. Blood pressure measurements may also be made by placing a blood pressure cuff around other limbs, such as a patient's thigh.

Blood pressure cuffs typically consist of a flexible, non-resilient casing having an internal pocket. The pocket normally contains a flexible, air-impermeable bladder. The casing also includes some type of locking device, such as VELCRO TM can be used to fasten the casing around the arm of the patient. Some newer blood pressure cuffs utilize a casing fabricated from an air permeable material, and they have an internal bladder thus making a separate bladder contained within an internal pocket unnecessary.

Once the cuff has been fastened around the arm of the patient, its bladder is inflated to occlude the brachial artery beneath the cuff. The pressure in the cuff is then gradually descreased, and the pressure at which blood begins to flow through the brachial artery at systole and diastole is noted to provide a reading of the patient's blood pressure.

While conventional blood pressure cuffs are satisfactory for most uses, they nevertheless suffer some limitations under various conditions. For example, it normally requires two hands to properly position and then snug a blood pressure cuff around the arm of a patient. It is therefore difficult, if not impossible, for some patients to take their own blood pressure, particulary where the patient's mobility is impaired. This disadvantage is becoming increasingly important in view of the increased use of automatic blood pressure monitoring in which blood pressure measurements can be made without the assistance of skilled medical practitioners.

In order to make it easier for blood pressure cuffs to be properly installed, particularly where they are self-installed, various type of automatic cuff installing and fastening devices have been developed. For example, one type of blood pressure cuff uses a small motor to place the cuff around the arm of a patient and an automatic latch to fasten the cuff in place. However, such automatic blood pressure cuffs are expensive and do not always work satisfactorily.

One conventional blood pressure cuff that can be automatically installed around the arm of a patient is available from Life Medical. The Life Medical cuff consists of a single resilient bladder lining the inner wall of a rigid cylindrical tube. A patients' arm is inserted into the tube and bladder until the tube and bladder are positioned over the brachial artery. The bladder is then inflated to occlude the brachial artery, and the pressure is then gradually reduced until the measurement has been completed.

One advantage of the Life Medical cuff is that it is self-snugging. It is not necessary for the cuff to be snugly placed around the arm of a patient because pressurization of the bladder performs the dual function of snugging the cuff against the patient's arm and occluding the brachial artery.

While the Life Medical cuff has the advantage of being self snugging, it is inherently incapable of performing accurate measurements because its bladder cannot be sized to perform the snugging function and still conform to the American National Standard ("ANS"). The ANS is the result of tests conducted to determine the optimum bladder size for obtaining accurate blood pressure measurement. The ANS specifies that a blood pressure cuff bladder should be 80 percent of the circumference of the arm on which it is installed. However, it is not possible for a blood presssure bladder extending all the way around an arm to be 80 percent of the circumference of the arm.

DISCLOSURE OF THE INVENTION

The primary object of this invention to provide a blood pressure cuff that is self snugging, yet is inherently capable of providing accurate blood pressure measurements.

It is another object of this invention to provide a self snuggging blood pressure cuff that can be used for patients having a wide range of arm diameters.

It is still another object of the invention to provide a blood pressure cuff of the character described that is relatively inexpensive and easy to use.

These and other objects of the invention are provided by a blood pressure cuff having a flexible, substantially non-resilient cylindrical casing with an air-impermeable measurement bladder and an air-impermeable snugging bladder. The casing has a circumference that is substantially larger than the circumference of a patient's limb on which it is adapted for use. The measurement bladder and the snugging bladder are isolated from each other so that the snugging bladder may be pressurized without pressurizing the measurement bladder. The casing is preferably formed with an air-impermeable material thereby integrally forming the measurement bladder and the snugging bladder. The dimensions of the measurement cuff should ideally conform to the American National Standard. A respective air-impermeable tube preferably extends from and communicates with each of the bladders so that the measurement bladder and the snugging bladder may be separately pressurized. The cuff may be used with either a manometer blood pressure measuring device or an automatic blood pressure monitor. The monitor preferably includes pressurizing means for pressurizing each of the bladders and then allowing fluid to bleed from the measurement bladder, a pressure transducer for measuring the pressure of the measurement bladder and measurement means for detecting the flow of the blood through an artery of the patient beneath the measurement bladder. The measurement means makes a blood pressure measurement as the pressurized fluid bleeds from the measurement bladder.

BEST MODE FOR CARRYING OUT THE INVENTION

Figure 1:
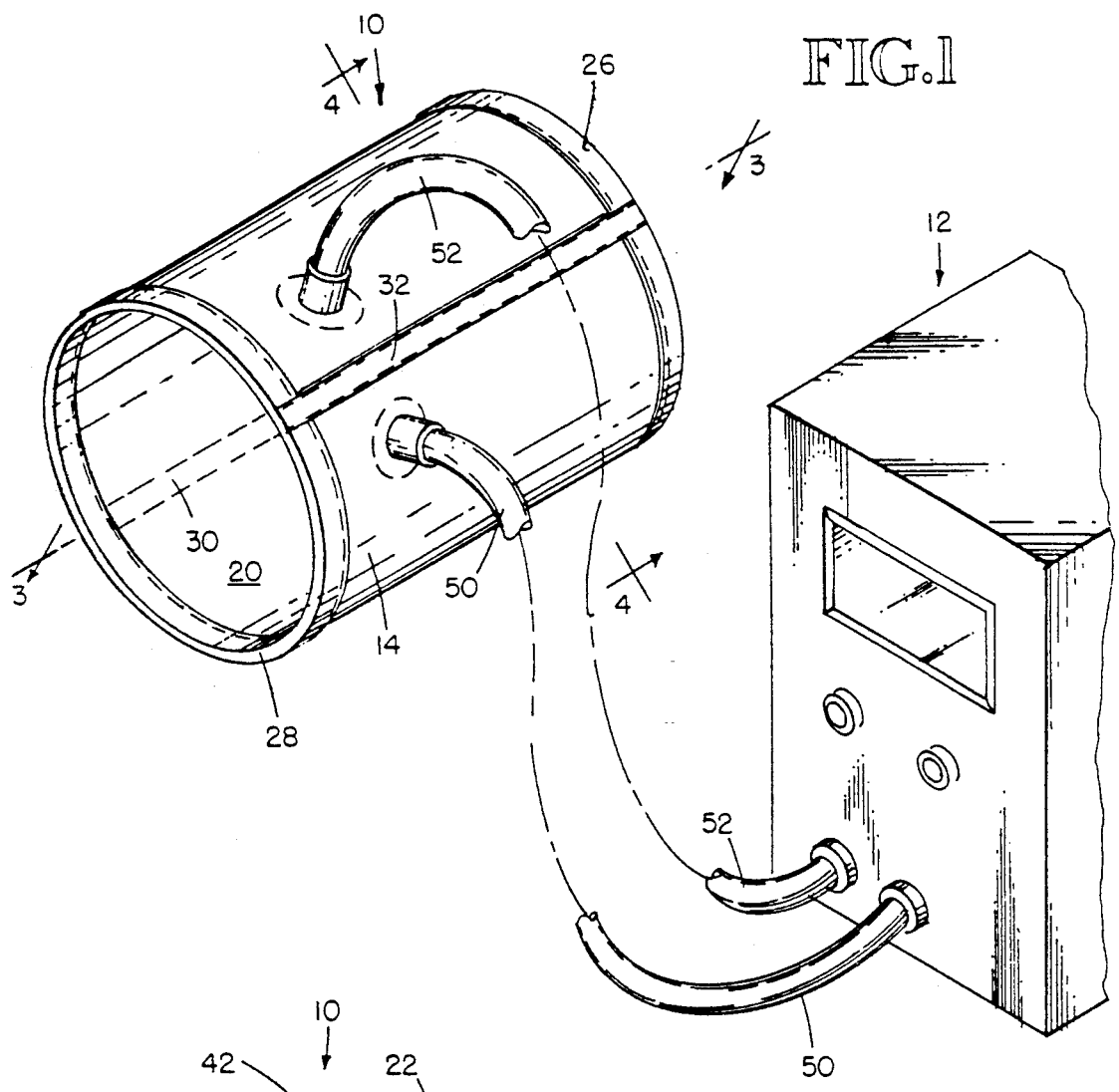
FIG. 1 is an isometric view of one embodiment of the inventive self-snugging universal blood pressure cuff shown connected to a blood pressure monitor.
Figure 2:
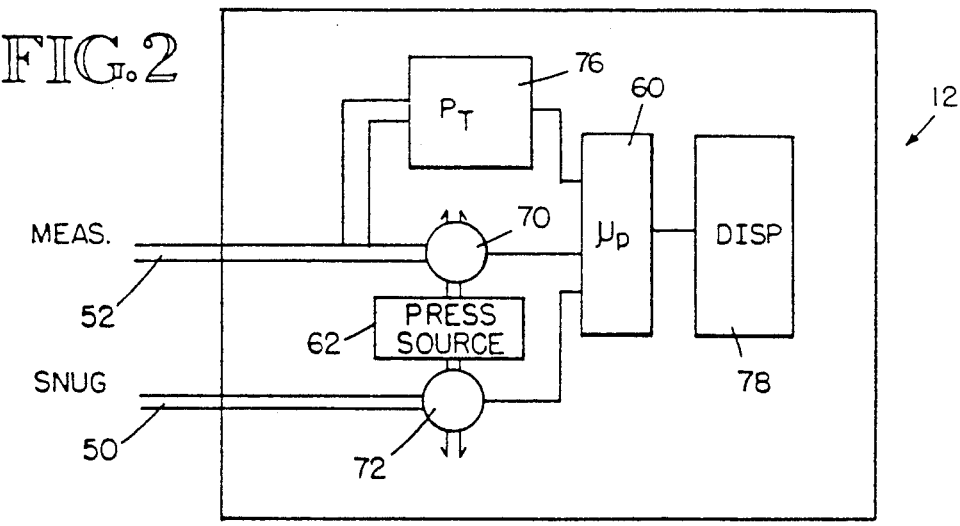
FIG. 2 is a block diagram of the blood pressure monitor illustrated in FIG. 1.

One embodiment 10 of the inventive self-snugging blood pressure cuff is illustrated in FIG. 1 connected to an automatic blood pressure monitor 12 illustrated in FIG. 2. The cuff 10 includes a casing 14 fabricated from a conventional, flexible, non-resilient, air-impermeable material. As further illustrated FIGS. 3 and 4, the casing 14 has a length L substantially equal to the length of conventional blood pressure cuffs and a total circumference $C_t$ that is substantially larger than the circumference of a patient's limb with which it is adapted for use. The casing 14 includes an inner cylindrical layer 20 and an outer cylindrical layer 22 which are joined to each other at the ends 26, 28 (FIGS. 1 and 4) and in two longitudinally extending strips 30, 32. The joining of the inner and outer layers 20, 22 to each other along the lines 30, 32 forms two circumferentially spaced bladders 40, 42. The bladder 40 is referred to herein as the "snugging bladder", while the bladder of 42 is referred to herein as the "measurement bladder". A first pneumatic tube 50 extends from the snugging bladder 40. A second pneumatic tube 52 extends from the measurement bladder 42. Since the bladders 40, 42 are pneumatically isolated from each other, they may be independently pressurized and depressurized through the tubes 50, 52.

Figure 3:
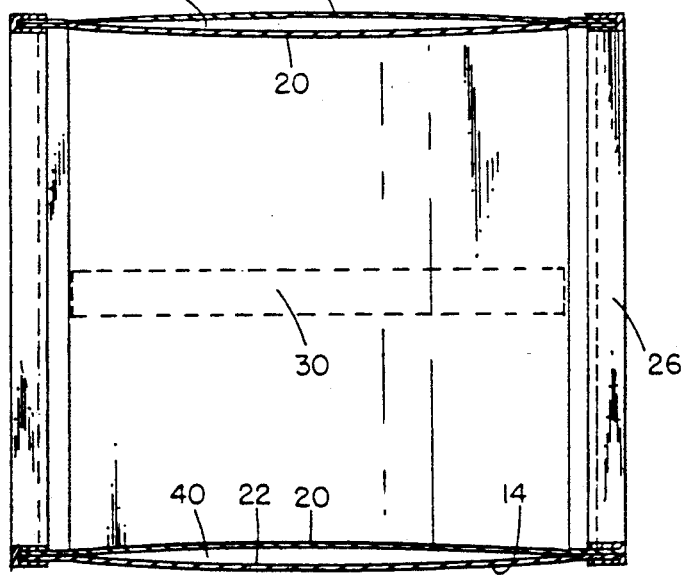
FIG. 3 is a cross-sectional of the blood pressure cuff of FIG. 1 taken along the line 3—3 of FIG. 1.
Figure 4:
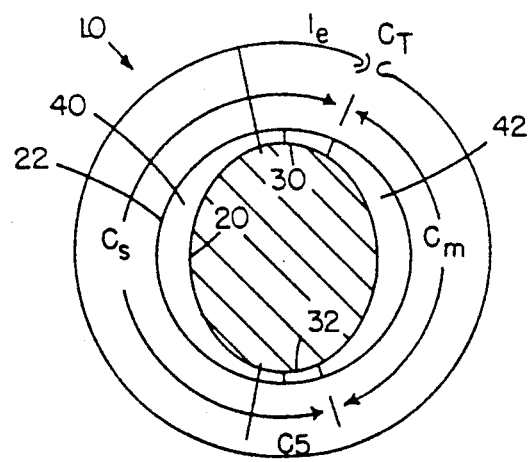
FIG. 4 is a cross-sectional of the blood pressure cuff of FIG. 1 taken along the line 4—4 of FIG. 1.

Although the preferred embodiment of the cuff 10 illustrated in FIGS. 1, 3 and 4 utilizes a casing 14 having integrally formed bladders 40, 42, it will be understood that other designs may be used. For example, a casing may have formed therein a pair of circumferentially spaced pockets containing separate measurement and snugging bladders.

The automatic blood pressure monitor 12 illustrated in FIG. 2 is primarily of conventional design. The monitor includes a conventional microprocessor 60 and a conventional air pressure source 62 such as, for example, an air pump supplying pressurized air to a tank. The pressure source 62 is connected through pneumatic tubing 64, 66 to electronically control pneumatic valves 70, 72 of conventional design. The valve 70 is connected to the pneumatic tube 52 communicating with the measurement bladder 42. The valve 72 is connected to the pneumatic tube 50 communicating with the snugging bladder 40. A conventional pressure transducer 76 measures the pressure in the measurement bladder 42 through the tube 52. The pressure transducer 76 provides an electrical output to the microprocessor 60, either directly or through a conventional analog-to-digital converter. The microprocessor 60 also controls the pneumatic valves 70, 72 and provides an output to a conventional display 78 indicative of the patient's blood pressure.

As mentioned above, the blood pressure monitor 12 is substantially indentical to commercially available blood pressure monitors. The only substantial difference is that it includes a second pneumatic valve 72 that applies air pressure to the snugging valve 40 before the start of a blood pressure measurement and then vents the snugging bladder 40 at the end a a blood pressure measurement.

Figure 5:
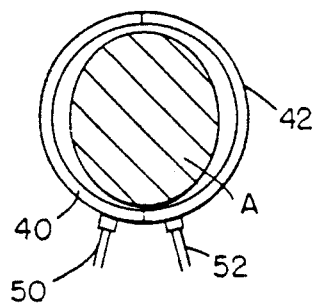
FIG. 5 is a cross-sectional schematic illustrating the invention blood pressure cuff in use with neither of its two bladders inflated.
Figure 6:
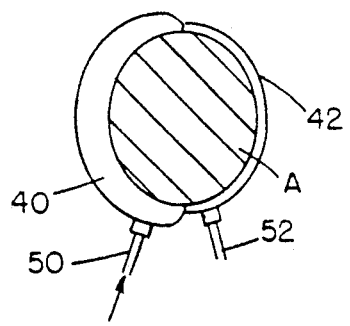
FIG. 6 is a cross-sectional schematic illustrating the inventive blood pressure cuff in use with only its snuggling bladder inflated.
Figure 7:
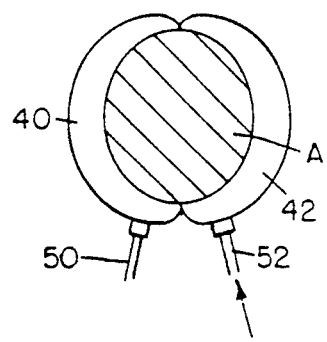
FIG. 7 is a cross-sectional schematic illustrating the inventive blood pressure cuff in use with both its snugging bladder and its measurement bladder inflated.

In operation, the arm A of a patient is inserted into the cuff 10 when it is uninflated as illustrated in FIG. 5. The uninflated length $C_t$ (FIG. 4) of the cuff is substantially larger than the circumference of the patient's arm A so that it may easily be slipped over the arm A of the patient. The microprocessor 60 then triggers the pneumatic valve 72, thereby connecting the pressure source 62 to the snugging bladder 40 through pneumatic tube 50. The snugging bladder 40 then inflates as illustrated in FIG. 6 so that the cuff can snugly surround the arm A of the patient. The microprocessor 60 then triggers valve 70 to connect the pressure source to the measurement bladder 42 through the pneumatic tube 52. The measurement bladder 42 is then inflated as illustrated in FIG. 7. Inflation of the measurement bladder 42 continues until the pressure in the measurement bladder 42, as indicated by the pressure transducer 76, reaches a a predetermined value. Microprocessor 60 then closes the pneumatic valve 70 and thereafter incrementally releases pressure from the measurement bladder 42 by periodically venting the pneumatic valve 70 for short periods. During the time that the pressure in the measurement bladder 42 is gradually reduced, the pressure in the measurement bladder 42 is measured by the pressure transducer 76. The pressure transducer 76 provides two types of information. First, it provides an indication of the pressure in the measurement bladder 42. Second, it provides an indication of oscillimetric pressure pulses that are used to detect the flow of blood through the brachial artery beneath the cuff 10. After sufficient air has been bled from the measurement bladder 42 to complete the measurement, the microprocessor 60 opens the valve 70 to vent the measurement bladder 42 and it opens the pneumatic valve 72 to vent the snugging bladder 50. The cuff 10 then assumes the configuration shown in FIG. 5 in which it may easily be removed from the arm A of the patient. Finally, the microprocessor 60 calculates the blood pressure in a conventional manner and provides appropriate signals to a conventional display 78.

With reference to FIG. 4, the size of the measurement bladder 42 preferably conforms to the American National Standard. According to the American National Standard, uninflated length $C_m$ of the measurement bladder 42 should be equal to 80% of the circumference of the patient's arm A. In the preferred embodiment, the uninflated length $C_m$ of the measurement bladder 42 is substantially equal to the length $C_s$ of the snugging bladder 40. Additionaly, the joints 30, 32 between the inner and outer layers 20, 22 have a width of about 0.1 $C_s$. Thus, the total uninflated circumference of the casing 14 is 2.2 $C_m$. Since $C_m$ equals 0.8 $C_a$ (where $C_a$ is the circumference of the patient's arm A), the total diameter of the casing 14 in the preferred embodiment is 2.2 $C_m$ equals 2.2 (times 0.8) $C_a$, or about 1.75 $C_a$. Thus, in the preferred embodiment, the uninflated circumference of the casing 14 is about 1¾ times the circumference of the patient's arm A, thereby providing more than adequate clearance to slip the cuff 10 over the patient's arm A.

Although the preferred embodiment of the invention utilizes a measurement bladder 42 having a size that is equal to the size of the snugging bladder 40, it will be understood that other dimensional relationships can be used. Thus, by providing a snugging bladder having a length that is shorter than the length of the measurement bladder, the uninflated circumference of the cuff can be made smaller than about 1.75 times the circumference of the patient's arm A. Other dimensional relationships will be apparent and can be used without departing from the scope of the invention.

The inventive blood pressure cuff thus provides a relatively inexpensive and simple device for allowing a blood pressure cuff to be easily installed on the arm or other limb of a patient. Furthermore, the snugging characteristics of the cuff do not in any manner degrade the accuracy of measurements that can be obtained by using the cuff.

I claim:

1. A self-snugging, universal blood pressure cuff, comprising a fexible, substantially non-resilient cylindrical casing having a circumference that is substantially larger than the circumference of a patient's limb which it is adapted for use, said casing having an air-impermeable measurement bladder and an adjacent air-impermeable snugging bladder circumferentially spaced from said measurement bladder, said measurement bladder and said snugging bladder being isolated from each other so that the pressure in said snugging bladder may be controlled independently from the pressure in said measurement bladder.

2. The self-snugging, universal blood pressure cuff of claim 1 wherein said casing is formed with an air-impermeable material, and wherein said measurement bladder and said snugging bladder are integral with said cuff 3. The self-snugging, universal blood pressure cuff of claim 1 wherein said measurement cuff has dimensions that substantially conform to the American National Standard.

4. The self-snugging, universal blood pressure cuff of claim 1 wherein a first air-impermeable tube extends from and communicates with said measurement bladder, and a second air-impermeable tube extends from and communicates with said snugging bladder so that said measurement bladder and said snugging bladder may be separately pressurized through said first and second tubes, respectively.

5. A system for measuring the blood pressure of a patient, comprising:
   a blood pressure cuff including:
   (a) a flexible, substantially non-resilient cylindrical casing having a circumference that is substantially larger than the circumference of a patient's limb which it is adapted for use,
   (b) an air-impermeable measurement bladder, and
   (c) an air-impermeable snugging bladder circumferentially spaced from and isolated from said measurement bladder; and
   blood pressure monitoring means including:
   installation pressurizing means connected to said snugging bladder for supplying a pressurized fluid to said snugging bladder responsive to a first trigger signal and for allowing said fluid to escape from said snugging bladder responsive to a second trigger signal;
   (b) measurement pressurizing means connected to said measurement bladder for supplying a pressurized fluid to said measurement bladder responsive to a third trigger signal and for then allowing said fluid to bleed from said measurement bladder;
   (c) pressure transducer means for measuring the pressure of the fluid in said measurement bladder;
   (d) measurement means operatively connected to said pressure transducer means for detecting the flow of blood through an artery of said patient beneath said measurement bladder and making a blood pressure measurement as said pressurized fluid bleeds from said measurement bladder; and
   (e) control means operatively connected to said installation pressurizing means, said measurement pressurizing means and said measurement means, for generating said first and third trigger signals at the start of a blood pressure measurement, and for generating said second trigger signal after said blood pressure measurement has been made.

6. The blood pressure measuring system of claim 5 wherein said casing is formed with an air-impermeable material, and wherein said measurement bladder and said snugging bladder are integral with said cuff.

7. The blood pressure measuring system of claim 5 wherein said measurement cuff has dimensions that substantially conform to the American National Standard.

8. The blood pressure measuring system of claim 5 wherein a first air-impermeable tube extends from said measurement bladder to said measurement pressurizing means, and a second air-impermeable tube extends from said snugging bladder to said installation pressurizing means so that said measurement bladder and said snugging bladder may be separately pressurized through said first and second tubes, respectively.

9. A method of measuring the blood pressure of a patient, comprising:
   placing a blood pressure cuff on a limb of said patient, said cuff including a flexible, substantially non-resilient cylindrical casing having a circumference that is substantially larger than the circumference of said limb, an air-impermeable measurement bladder, and an air-impermeable snugging bladder circumferentially spaced from and isolated from said measurement bladder;
   supplying a pressurized fluid to said snugging bladder until the casing of said cuff is snug around the arm of said patient;
   supplying a pressurized fluid to said measurement bladder;
   allowing said fluid to slowly bleed from said measurement bladder;
   measuring the pressure of the fluid in said measurement bladder as said fluid slowly bleeds from said measurement bladder;
   detecting the flow of blood through an artery beneath said measurement bladder as said pressurized fluid bleeds from said measurement bladder thereby making a blood pressure measurement; and
   allowing said fluid to escape from said snugging bladder thereby disengaging said cuff from the limb of said patient.

10. The method of claim 9 wherein said measurement cuff has dimensions that substantially conform to the American National Standard.

* * * * *